United States Patent [19]

Sanchez et al.

[11] Patent Number: 6,068,823
[45] Date of Patent: May 30, 2000

[54] PROCESS FOR THE BENIGN DIRECT FIXATION AND CONVERSION OF NITROGEN OXIDES

[75] Inventors: Ramiro Sanchez; Graciela Lubertino, both of Houston, Tex.

[73] Assignee: The University of Houston System, Houston, Tex.

[21] Appl. No.: 09/231,751

[22] Filed: Jan. 15, 1999

[51] Int. Cl.$^7$ .................. B01D 53/56; C07C 243/02; C07C 243/04
[52] U.S. Cl. .................. 423/235; 423/239.1; 252/182.3; 252/182.12; 556/422; 564/107; 564/112
[58] Field of Search ............................ 252/182.3, 182.12; 556/422; 423/235, 239.1; 564/107, 112

[56] References Cited

U.S. PATENT DOCUMENTS

| | | | |
|---|---|---|---|
| 3,957,823 | 5/1976 | Seebach et al. | 564/112 |
| 4,944,894 | 7/1990 | Mehta et al. | 252/182.3 |
| 5,002,689 | 3/1991 | Mehta et al. | 252/182.12 |
| 5,320,774 | 6/1994 | Mehta et al. | 252/182.12 |

FOREIGN PATENT DOCUMENTS 282419   9/1988   European Pat. Off. .

*Primary Examiner*—Tom Dunn
*Assistant Examiner*—Peter DiMauro
*Attorney, Agent, or Firm*—Robert W. Strozier

[57] ABSTRACT

A direct fixation of $NO_2$ and $N_2O_4$ at room temperature and atmospheric pressure is described using bis(diorganoamino) magnesium compounds formed from reactions between donor-solvent free diorganomagnesium compounds and primary or secondary amines, yielding new compositions of matter having the general formulas $[(R_2N)_i(R_2NN_xO_y)jMg]_m$ and $[(R_2N)_i(R_2NN_xO_y)_j(N_xO_y)_kMg]_m$. Methods are also described to convert these new compositions of matter into useful organic compounds and nitrogen gas.

20 Claims, No Drawings

PROCESS FOR THE BENIGN DIRECT FIXATION AND CONVERSION OF NITROGEN OXIDES

BACKGROUND OF THE INVENTION

1. Field of the Invention

The present invention relates to a process for the benign direct fixation and conversion of nitrogen oxides at room temperature and atmospheric pressure to nitrogen oxide clean effluent streams or to useful organic compounds and intermediates.

More particularly, the present invention relates to a process for reacting nitrogen oxides with bis(diorganoamino) magnesium compounds at room temperature and ambient pressures to generate nitrogen oxide free effluent streams or synthetically valuable intermediates. The invention also relates to novel intermediates and processes for their use.

2. Description of the Related Art

Unlike aminomagnesium halides $R_2NMgX$, first reported by Bodroux (Bodroux in *Bull. Soc. Chim.,* 33, 831, (1905)) and then made synthetic popular by Hauser (Hauser and Walker, *J. Am. Chem. Soc.,* 69, 295, (1947)), Bis (diorganoamino)magnesium compounds $[(R_2N)_2Mg]_n$, which can be prepared by reacting primary and secondary amines and donor-solvent free diorganomagnesium compounds, have been found to possess quite different structures. These compounds have also been found to bring about very different and unexpected chemical transformations see for example: U.S. Pat. No. 4,944,894; Sanchez, R and Scott, W., *Tetrahedron Letters,* 29, 139, (1988); Sanchez, R., Vest, G., Scott, W., and Engel, P. S., in *J. Org. Chem.,* 54, 4026, (1989); Sanchez, R., Vest, G. and Despres, L., *Synth. Comm.,* 19, 2909, (1989)and Sanchez, R., and Felan, O., *Main Group Metal Chemistry,* 18, No. 4, 225, (1995), incorporated herein by reference.

Because fixation of $NO_2$ and $N_2O_4$ is a very important industrial process and current methods utilizing nitrogen containing compounds all involve extremely forcing and or brutal reaction conditions or have other major limitations such as the processes described in U.S. Pat. Nos. 5,120,516; 5,264,195; 4,877,590; 4,943,421; 3,784,478; 3,034,853; and 3,044,844, (incorporated herein by reference) there is a need in the art for a novel benign process for the removal of nitrogen oxides including $NO_2$ and $N_2O_4$ from industrial effluent streams.

SUMMARY OF THE INVENTION

The present invention provides a method for the direct fixation and conversion of nitrogen oxides into useful synthetic organic reagents under conditions sufficient to promote the fixation of nitrogen oxides. The process involves contacting a magnesium amide with nitrogen oxides where the nitrogen oxides are generally in components of a gas stream containing other constituents. The magnesium amides react with the nitrogen oxides to form magnesium amide-nitrogen oxide complexes which can be converted into nitrogen gas and nitrogen-free combustible organic compounds. Thus, the magnesium amides convert an effluent or waste stream containing noxious components to an effluent containing readily combustible hydrocarbons or oxygenated hydrocarbons.

The present invention also provides a method for producing synthetically useful reagents by contacting a magnesium amide with a source of nitrogen oxides, again producing intermediate amide-nitrogen oxide magnesium complexes. However, the complexes are converted into synthetically useful organic intermediates including nitrosamines and their derivatives instead of combustible hydrocarbons. The present invention also provides a method for the conversion of nitrogen oxides to oxygenated compounds by contacting, a magnesium amide with nitrogen oxides under conditions sufficient to promote nitrogen oxide fixation followed by protonation.

The present invention further provides novel intermediates formed by the reaction of magnesium amide with nitrogen oxides.

DETAILED DESCRIPTION OF THE INVENTION

The inventors have found that nitrogen oxides contained in waste streams can be converted to either nitrogen gas and combustible nitrogen-free hydrocarbons or oxygenated hydrocarbons or synthetically useful reagents by contacting the nitrogen oxides with a magnesium amide under conditions sufficient to promote nitrogen oxide fixation. The magnesium amides react with nitrogen oxides to form intermediate reaction complexes. The complexes are thought to occur primarily via an insertion reaction where a nitrogen oxide molecule is inserted between the nitrogen-magnesium bond of the magnesium amide, although direct or secondary displacement reactions may also be competitive. These complexes are then convertible into either nitrogen gas and nitrogen-free combustible organic compounds or into synthetically useful organic compounds such as nitrosamines or their derivatives or oxygenated hydrocarbons.

Broadly, the method of the present invention involves contacting a bis(diorganoamino)magnesium ("magnesium amide") compound of general formula (I):

$$[(R_2N)_2Mg]_n \qquad (I)$$

with a nitrogen oxide of the general formula (II):

$$N_xO_y \qquad (II)$$

to form a new class of comprising intermediates of the general formula (III):

$$[(R_2N)_i(R_2NN_xO_y)_jMg]_m \qquad (III)$$

under suitable reaction conditions, where:

the R groups are the same or different and are hydrogen atoms, linear or branched carbon containing groups or linear or branched silicon containing groups;

i is a number having a value less than 2.0 (i<2.0);

j is a number having a value greater than 0.0 and less than or equal to 2.0 (0.0<j≦2.0);

n is an integer having a value between 1 and infinity (1≦n≦∞);

m is an integer having a value between 1 and infinity (1≦m≦∞);

x is an integer having a value between 1 and about 8; and y is an integer having a value between 1 and about 16.

The integers n and m of the magnesium amides of formula (I) and the intermediates of formula (III) can range from 1 to infinity because these species can exist as uni-molecular species or as infinitely extended polymeric structure depending on the nature of R, reaction conditions, solvents, etc. Although m can range from 1 (unimolecular species) depending on the nature of R and/or solvent to infinity in their neat form, in poor solvents, solids or semi-solids, preferred ranges for the integers n and m are between 1 and about 10,000, and particularly, between 1 and about 1,000 and especially between 1 and about 500 and most especially between 1 and about 100. Of course, n and m are independent of each other and their exact numeric value will depend on the nature of the starting magnesium amide, the composition of the nitrogen oxide, the nature of R, the extent of reaction, the solvent, the temperature, the pressure and other common factors that control aggregation.

The positive real numbers i and j vary within their indicated ranges to indicate partial to complete reaction between the magnesium amides and nitrogen oxide species. If the reaction follows a pure insertion mechanism and goes to completion, then i will be equal to 0.0 and j will be equal 2.0, because two molecules of nitrogen oxide can react with each molecule of formula (I). However, if some displacement reactions occur as well, then the final molecular repeating unit may not be precisely $(R_2NN_xO_y)_2Mg$ because some of the $R_2N$ moieties will have been replaced by $N_xO_y$ moieties.

After formation of the intermediates of formula (III), these intermediates can be converted to a desired reaction product. For nitrogen oxide removal and post oxidation processing of waste gas streams containing nitrogen oxides, the intermediates of formula (III) are converted into nitrogen and nitrogen-free combustible organic compounds.

Alternatively, the intermediates of formula (III) can be converted into a reaction product comprising nitrosamines which can be isolated or the intermediates of formula (III) can be converted into a reaction product comprising mixtures of compounds derived from in situ formed complexes depending on the nature of R. Nitrogen is generally been expelled as nitrogen gas. Such work-up can include treating the reaction mixture with acids, bases or other reagents to affect a desired chemical transformation of in situ formed complexes. To produce oxygenated compounds derived from the in situ formed complexes, the transformation involves acid or base hydrolysis, preferably, dilute acid or base hydrolysis. The intermediates of formula (III) can generally be converted into alkanes, olefins, carbocyclic and heterocyclic aromatic compounds and substituted heterocyclic and carbocyclic compounds, aldehydes, ketones, carboxylic acids and carboxylic acid derivatives, oximes, N-nitroso compounds, N-oxide amines, nitrosamines or the like. If the intermediates for formula (III) are derived from silicon containing magnesium amides, then the intermediates can generally be converted into silanes, silenes, silocarbocyclic and heterocyclic compounds including aromatic compounds, siloxanes, N-nitroso and N-oxide silicon containing compounds, aldehydes, ketones, carboxylic acids and carboxylic acid derivatives, oximes of silicon containing compounds.

The contacting step involving the magnesium amides and nitrogen oxides is preferably carried out in a condensed phase, i.e., solid or liquid. Solids include cakes, beds, beads, coated beds, other solid shapes or the like. The solids can also be in the presence of inert supports, binders or carriers. Liquid include liquids (e.g., low melting or molten magnesium amides), solutions, slurries, dispersions, emulsions, or the like where the solutions, slurries, dispersions, emulsions are formed in the presence of a suitable solvent or solvent mixture at all concentrations.

The contacting step occurs efficiently at ambient temperature and atmospheric pressure; however, the contacting can be carried out at higher temperatures and pressures keeping in mind the general consequences of increasing either temperature and/or pressure on reaction dynamics and competitive kinetics.

Additionally, the transformation reaction or post contacting reaction steps, such as hydrolysis, are generally carried out in a condensed phase, especially a liquid phase (liquids, molten liquids, solutions, dispersions, emulsions, or the like), in the presence or absence of a suitable solvent or solvent mixture and at ambient temperature and atmospheric pressure. However, these transformation reactions can also be carried out at higher temperatures and pressures keeping in mind the general consequences of increasing either temperature and pressure on reaction dynamics and competitive kinetics.

The starting magnesium amides of formula (I) are formed by contacting a diorganomagnesium compound with a primary or secondary amine. Generally, this reaction is also carried out in a condensed phase using a donor-free solvent, i.e., a solvent that does not have strong electron donating capabilities or is not a strong Lewis base. The scope and versatility of the magnesium amide formation reaction is generally disclosed in the following publications: U.S. Pat. No. 4,944,894; Sanchez, R and Scott, W., *Tetrahedron Letters,* vol. 29, 139, (1988); Sanchez, R., Vest, G., Scott, W., and Engel, P.S., *J. Org. Chem.,* 54, 4026, (1989); Sanchez, R., Vest, G. and Despres, L., *Synth. Comm.,* 19, 2909, (1989) and Sanchez, R., and Felan, O., *Main Group Metal Chemistry,* 18, No. 4, 225, (1995), incorporated herein by reference.

The present invention is also directed to a new class of intermediates comprising compounds of the general formula (III):

where:

the R groups are the same or different and are hydrogen atoms, carbon containing groups or silicon containing groups;

i is a number having a value less than 2.0 (i<2.0);

j is a number having a value greater than 0.0 and less than or equal to 2.0 (0.0<j≦2.0);

m is an integer having a value between 1 and infinity (1≦m≦∞);

x is an integer having a value between 1 and about 8; and y is an integer having a value between 1 and about 16.

A preferred sub-class of intermediates comprise compounds of formula (IIIa):

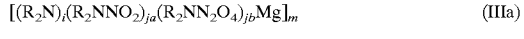

where:

the R groups are the same or different and are hydrogen atoms, carbon containing groups or silicon containing groups;

i is a number having a value less than 2.0 (i<2.0); ja and jb are numbers, the sum of which is greater than 0.0 and less than or equal to 2.0 (0.0<ja+jb≦2.0); and m is an integer having a value between 1 and infinity (1≦m≦∞).

Another preferred sub-class of intermediates comprise compounds of formula (IIIb):

where:

the R groups are the same or different and are hydrogen atoms, carbon containing groups or silicon containing groups;

i is a number having a value less than 2.0 (i<2.0);

j is a number having a value greater than 0.0 and less than or equal to 2.0 (0.0<j≦2.0); and m is an integer having a value between 1 and infinity ($1 \leq m \leq \infty$).

And yet, another preferred sub-class of intermediates comprise compounds of formula (IIIc):

$$[(R_2N)_i(R_2NN_2O_4)_j Mg]_m \qquad (IIIc)$$

where:

the R groups are the same or different and are hydrogen atoms, carbon containing groups or silicon containing groups;

i is a number having a value less than 2.0 ($i < 2.0$);

j is a number having a value greater than 0.0 and less than or equal to 2.0 ($0.0 < j \leq 2.0$); and m is an integer having a value between 1 and infinity ($1 \leq m \leq \infty$).

Because the reaction between the magnesium amide of formula (I) and nitrogen oxides is thought to occur primarily via an insertion reaction, the preferred value for i and or the combination of i and j is 2.0 under stoichiometric reaction conditions, i.e., two moles of nitrogen oxide per mole of magnesium amide. Of course, as the reaction proceeds, the values of i and j will change continuously to some final value that will depend on the amount of starting magnesium amide and the amount of nitrogen oxides fed to the magnesium amide.

If displacement reactions and insertion reactions occur concurrently, then the resulting complexes can be represented by compounds of formula (IV):

$$[(R_2N)_i(R_2NN_xO_y)_j(N_xO_y)_k Mg]_m \qquad (IV)$$

where:

the R groups are the same or different and are hydrogen atoms, carbon containing groups or silicon containing groups;

i is a number having a value less than 2.0 ($i < 2.0$);

j is a number having a value greater than or equal to 0.0 and less than or equal to 2.0 ($0.0 \leq j \leq 2.0$);

k is a number having a value less than 2.0 ($k < 2.0$);

m is an integer having a value between 1 and infinity ($1 \leq m \leq \infty$);

x is an integer having a value between 1 and about 8; and y is an integer having a value between 1 and about 16.

Preferred compounds of formula (IV) are those where i and k are about 0.0 and j is about 2.0. Of course, i represent the extent of the insertion reaction minus displacement reaction while k represents the extent of the displacement reaction.

The magnesium amides of formula (I) can be used as a homogenous solution or heterogeneous mixture, such as a dispersion, emulsion, slurry, or the like, in a suitable solvent. Thus, the solubility of the magnesium amides of formula (I) in the solvent is not critical and may vary over a wide range from infinitely soluble to totally insoluble.

If the nitrogen oxide is associated with a flue gas stream or other effluent (gaseous or otherwise), then the reaction can be carried out in a number of different manners where the magnesium amide acts as a scavenger converting nitrogen oxides to nitrogen-free, combustible organic compounds derived from the R group of the magnesium amides.

One such manner to scavenge nitrogen oxides is to use a counter-flow reactor where the gaseous effluent stream rises through a continuous scavenger stream containing the magnesium amide. The scavenger stream is then reacted with an alcohol or the starting amine under acidic conditions to protonate the intermediates of formulas (III) and (IV) to nitrogen gas and nitrogen-free, combustible organic compounds derived from the R groups. If an alcohol is used, then the reaction conditions can be adjusted so that the starting magnesium amides of formula (I) react much slower than the intermediates of formulas (III) and (IV). The resulting nitrogen-free, combustible organic compounds derived from the R groups can be separated from the magnesium alkoxides and the magnesium amides and burned to carbon dioxide and water (efficient combustion), while the magnesium alkoxides and unreacted magnesium amides stream can be reacted with starting amine to regenerate the magnesium amide. This stream can then be stripped of alcoholic solvent and recycled to the magnesium feed stream. Of course, upstream of the counter-flow reactor, a magnesium amide forming reactor can be used to combine the diorganomagnesium with a desired primary or secondary amine.

Alternatively, the magnesium amide can be used in a solid, semi-solid, liquid or molten form and the nitrogen oxide containing stream can be passed through or over the magnesium amide. If the magnesium amide is a solid or supported solid, then the scavenger reactor can consist of several fixed bed columns that are periodically reacted with a hydrolysis agent such as an acid alcohol wash or an amine wash which would liberate nitrogen gas and nitrogen-free, combustible hydrocarbons which can be forwarded to a combustion zone or recovered. The protonated bed can then be regenerated by reacting the bed with fresh amine. The liberated alcohol, if alcohol is used, can then be recovered and recycled.

Preferred scavenger magnesium amides for converting nitrogen oxides into nitrogen gas and nitrogen-free, combustible organic compounds include cycloalkylamines, alkyl amines, polycyclic aromatic amines or the like. Particularly preferred amines include 2-(1-cyclohexenyl)-ethylamine, myrtanylamine, naphthyl amine, cyclohexyl amine, or the like.

Suitable supports include, without limitation, any inert support, binder or carrier such as silica, alumina, magnesia, titania, aluminosilicas, aluminates, silicates, aluminophosphates, zeolites, silicalites, or any other similar support, binder or carrier known in the art. Moreover, the magnesium amide can be deposited on a monolith like those used in catalytic converters. Furthermore, the magnesium amides can be used as a component in catalysts used in catalytic converters for automobiles, provided that the magnesium amides is periodically regenerated and the converters are supplied with a combustible reagent that can hydrolyze the intermediates of formulas (III) and (IV) to nitrogen gas and nitrogen-free, combustible organic compounds.

Any other continuous or non-continuous reactors and reactor systems can be used as is well-known in the art such as an autoclave reactors, stirred tank reactors, plug-flow reactors, continuous stirred tank reactors, segmented reactors or the like. Moreover, if the reaction is carried out substantially in the absence of an oxygen containing gas (flue-gases are generally greatly depleted in oxygen), then the nitrogen gas formed in the reaction can be recovered and used.

One preferred process involves contacting a scavenger comprising compounds of formula (I):

$$[(R_2N)_2 Mg]_n \qquad (I)$$

with a waste stream comprising compounds of formula (II):

$$N_xO_y \qquad (II)$$

to form a reaction mixture comprising intermediates of formulas (III) and (IV):

$$[(R_2N)_i(R_2NN_xO_y)_j Mg]_m \qquad (III)$$

$$[(R_2N)_i(R_2NN_xO_y)_j(N_xO_y)_k Mg]_m \qquad (IV)$$

and an unreacted portion of the compounds of formula (I) under reaction conditions sufficient to facilitate the formation of the intermediates of formulas (III) and (IV) where R, i, j, k, n and m are as previously defined. The reaction mixture is then separated into an intermediate product comprising the compounds of formulas (III) and (IV) and unreacted compounds of formula (I). The unreacted compounds of formula (I) can be recycled and combined with the scavenger of in the contacting step described above. The intermediate product can be hydrolyzed to a magnesium containing product and a nitrogen-free product comprising nitrogen-free derivative of R. The magnesium containing product can be reacted with a starting amine of formula $R_2NH$ to form regenerated magnesium amide which can be combined with the scavenger of the contacting step. The nitrogen-free product can then be burned in the presence of an oxidizing agent (preferably air or oxygen) to form a combustion product comprising carbon dioxide and water substantially free of incomplete combustion products such as carbon monoxide, incomplete hydrocarbon combustion products or the like.

The contacting step can involve contacting to fluid streams, a liquid stream and a solid or semi-solid, a solid or semi-solid and a gas stream or a gas stream and a liquid stream where liquid has the meaning given herein.

Suitable solvents for making the magnesium amides include, without limitation, any hydrocarbon solvent or halogenated solvent. The term hydrocarbon solvent designates solvents comprised primarily of hydrogen and carbon such as aliphatic solvents, cyclo-aliphatic solvents or aromatic solvents. Non-limiting illustrative examples of aliphatic solvents include pentanes, hexanes, heptanes, octanes, dodecanes, gasolines and other petroleum fractions and unsaturated analogs thereof, or mixture or combinations thereof. Non-limiting illustrative examples of the cyclo-aliphatic solvents include cyclo-alkanes such as cyclopentane, cyclohexane, cycloheptane, cyclooctane, or the like, derivatives thereof and unsaturated analogs thereof, or mixture or combinations thereof. Non-limiting illustrative examples of aromatic solvents include benzene, toluene, xylenes, naphthalene or the like, derivatives thereof and unsaturated analogs thereof, or mixture or combinations thereof. The term halogenated solvent designates solvents comprising primarily hydrogen, carbon and halogen (F, Cl, Br, and I) or primarily carbon and halogen such as halogenated and perhalogenated aliphatic solvents, cyclo-aliphatic solvents or aromatic solvents. Non-limiting illustrative examples of halogenated aliphatic solvents include methylene chloride, methylene bromide, bromochloromethane, chloroform, trichloroethane, trichloroethene, carbontetrachloride, CFCs, fluorocarbons, halogenated pentanes, hexanes, heptanes, octanes, dodecanes, or the like or mixture or combinations thereof. Non-limiting illustrative examples of halogenated cyclo-aliphatic solvents include halogenated cyclo-alkanes, derivative thereof and unsaturated analogs thereof, or mixture or combinations thereof. Non-limiting illustrative examples of aromatic solvents include chlorobenzene, chlorotoluenes, chloroxylenes, or the like, derivative thereof and unsaturated analogs thereof, or mixture or combinations thereof.

Suitable solvents for carrying out the contacting reaction between compounds of formula (I) and compounds of formula (II) include, without limitation, hydrocarbon solvents, halogenated hydrocarbon solvents, or donor solvents or mixtures thereof. The term hydrocarbon solvent and halogenated hydrocarbon solvent have the same meaning as set forth above. The term donor solvent designates any solvent capable of donating electron density to a Lewis acid, i.e., a Lewis base. Non-limiting illustrative examples include ethers, tertiary amines, sulfoxides, and any other compound which can donate electron density to an electron deficient center or site of a molecule, especially compounds that contain an electronegative atom such as nitrogen, oxygen, phosphorus, sulfur, or the like.

Preferred solvents, hydrocarbon or donor, are those having between about 5 and about 25 carbons atoms. More preferred are solvents having between about 5 and about 12 carbons atoms and having a boiling point between about 50 and about 200° C.

Suitable primary and secondary amines used to form the magnesium amides of formula (I) include, without limitation, any amine of formula (V):

Suitable R groups include, without limitation, a hydrogen atom, a carbon containing group, a silicon containing group or mixture thereof. Suitable carbon containing groups include, without limitation, hydrocarbyl groups such as alkyl, alkenyl, or aryl, groups or substituted and heteroatom analogs thereof or the like. Suitable silicon containing groups include, without limitation, silylhydrocarbyl groups such as silylalkyl, silylalkenyl, or silylaryl groups or substituted and heteroatom analogs thereof. Substituted analogs include R groups bearing alkoxy substituents, secondary amino substituents, halogen atom substituents, SR' substituents, PR'$_2$ substituents where R' is a group coextensive with R or the like. Heteroatom analogs in the case of carbon containing and silicon containing groups include N, O, S, P or the like. Preferably, the R groups are hydrogen atoms or groups having between about 4 and about 50 atoms.

Suitable reaction conditions for contacting compounds of formula (I) with nitrogen oxides of formula (II) include any reactions conditions sufficient to facilitate the reaction. Preferably, the contacting is carried out at room temperature and atmospheric pressure, but higher and lower temperatures and pressures can be used as well. In fact, if the supply of nitrogen oxides derives from flue-gas, then the reaction can be performed at the temperature and pressure of the flue-gas.

Suitable acids and bases for carrying out post reaction protonation include, without limitation, any inorganic or organic acid or base that will protonate intermediates of formulas (III) and (IV) or the in situ derived complexes to alcohols and carbonyl derivatives thereof, nitro compounds, nitrosamines, and nitrogen-free hydrocarbon. Preferred acids include mineral acids such as HCl, HBr, $H_2SO_4$, $H_3PO_4$, boric acid, or the like or low molecular weight organic acids such as carbonic acid, formic acid, acetic acid, propanoic acid, or the like. Preferred bases include metal hydroxides such as NaOH, KOH, or the like or primary or secondary amines and low molecular weight carboxylic acids such as sodium or potassium bicarbonate, sodium or potassium carbonate, sodium or potassium formate, sodium or potassium acetate, sodium or potassium propionate, or the like.

EXAMPLES

The following examples are included for the sake of completeness of disclosure and to illustrate the methods of making the compositions and composites of the present invention as well as to present certain characteristics of the compositions, but in no way are these examples included for the sake of limiting the scope or teaching of this disclosure.

Example 1

This example illustrates the reaction between bis[2-(1-cyclohexenyl) ethylamino]magnesium and $NO_2/N_2O_4$.

Into an airless-ware flask previously flushed with argon gas were added 50 mL (35.5 mmol) of a 0.71 M solution of dibutylmagnesium in n-heptanes, via syringe through a septum mounted on the reaction flask. Argon flow to the flask was stopped while 10 mL (71 mmol) of 2-(1-cyclohexenyl) ethylamine was added drop wise to the dibutylmagnesium solution. The evolution of off-gases during the reaction was monitored visually at the exit bubbler. During the reaction a yellow solid forms immediately, the flask and content became warm to the touch, but the rise in temperature was not quantified. The reaction mixture was then allowed to react for an additional 24 h at room temperature.

After this reaction period, nitrogen dioxide was bubbled through a Tygon tubing connected to a cylinder inserted to the reaction flask via the rubber septum. During the reaction more solid was formed and the color changed to orange. The addition of nitrogen dioxide continue for two days. After this period, the reaction mixture was hydrolyzed by adding 20 mL of hydrochloric acid (10% by volume) and 40 mL of water. After hydrolysis, the pH of the reaction mixture was basic. Next, the reaction solution was extracted three times with 30 mL of ether.

The products from both layers (organic and aqueous) were identified using GC/MS.

Aqueous layer: 1-ethylcyclohexene; cyclohexanone; methylcyclohexane; 2-(1-cyclohexenyl)ethylamine.

Ether layer: 2-(1-cyclohexenyl)ethylamine; 1,4-bis (methylene) cyclohexane; dimethyl hexanadioate.

After addition of HCl (10%) to neutralize the solution:

Aqueous layer: 3-methylcyclohexene; 1-methylcyclohexene; cyclohexanone; E,Z-3-ethylidencyclohexene; 2-(1-cyclohexenyl) ethylamine.

Ether layer: 1-methylcyclohexene; E,Z-3-ethylidencyclohexene; 2-(1-cyclohexenyl) ethylamine; 3-ethylcyclohexanone; 1,2,3,4-tetrahydroquinoline.

Example 2

This example illustrates the reaction between bis(1-adamantanamino)magnesium and $NO_2/N_2O_4$.

Into a 200 mL airless-ware flask previously purged with argon gas were placed 4.3 g (28.4 mmol) of 1-adamantanamine. Argon flow to the flask was stopped and 20 mL (14.2 mmol) of dibutylmagnesium of 0.71 M concentration was added dropwise. The reaction mixture was allowed to react for 24 hr. The evolution of gases was observed at the exit bubbler. Then, addition of nitrogen dioxide started using a Tygon tubing inserted into the reaction flask via the rubber septum. This addition continue for two days, after which the solid changed colors from white to orange. The hydrolysis was done adding 20 mL of hydrochloric acid (10% by volume), and 40 mL of water, after which the pH of the solution was acid, then sodium bicarbonate (saturated solution) was added to neutralize the solution before the extraction with ether. Next, the mixture was extracted three (3) times with 30 mL of ether. The products from both layers were identified using GC/MS.

Aqueous layer: 1-adamantanol; 1-chloro-adamantane; tricyclo[3.3.1.13,7] decan-1-amine; 1-carboxylic acid adamantane.

Ether layer: adamantane; 1-adamantanol; 1-chloro-adamantane; 1-nitrosoadamantane.

Example 3

This examples illustrates the reaction between bis(N,N-diphenylamino)magnesium and $NO_2/N_2O_4$.

Into a 200 mL airless-ware flask previously purged with argon were placed 12.2 g (71 mmol) of diphenylamine. After the introduction of the diphenylamine, the reaction flask was flushed for an additional 15 min period with argon to insure the removal of any additional oxygen from the reaction vessel. Argon flow to the flask was stopped while 50 mL (35.5 mmol) of a 0.71 M solution of dibutylmagnesium in n-heptane were added dropwise via syringe through a septum mounted on the flask containing the diphenylamine. The evolution of off-gases during the reaction was monitored visually at the exit bubbler. During the reaction, the flask and contents became warm to the touch but no measurement of the rise in temperature was quantified. The resultant product magnesium amide precipitated as a white solid when stirring was stopped. The reaction mixture was then allowed to stir at room temperature for an additional 24 h period under an argon atmosphere.

After this reaction period, the reaction flask was connected to a nitrogen dioxide cylinder via a Tygon tubing that was inserted in the reaction flask through the rubber septum. The nitrogen dioxide gas was bubbled into the reaction flask for 2 days.

Hydrolysis of the products was done using 20 mL of hydrochloric acid (10% by volume), and 40 mL of water. After this the pH was acidic, the reaction mixture was then neutralized with sodium bicarbonate (saturated solution). The reaction mixture was extracted three times with 30 mL of ether.

The products from both layers were identified using GC/MS.

Aqueous layer: 2-nitro-N-phenyl-benzenamine; diphenyl amine.

Ether layer: 2-nitro-N-phenyl-benzenamine; diphenyl amine.

Example 4

This example illustrates the reaction between bis(N,N-diisopropylamino)magnesium and $NO_2/N_2O_4$.

Into a 200 mL airless ware flask previously flushed with argon gas were transferred 50.0 mL (35.5 mmol) of a 0.71 M solution of dibutylmagnesium via syringe through a septum mounted on the reaction flask. Argon flow to the flask was stopped while 10.0 mL (72 mmol) of diisopropylamine was added dropwise to the dibutylmagnesium solution. The evolution of off-gases during the reaction was monitored visually at the exit bubbler. During the reaction, the flask and contents became warm to the touch but no measurement of the rise in temperature was quantified. The reaction mixture was then allowed to react at room temperature for an additional 24 h. After this reaction period, the reaction flask was connected to a nitrogen dioxide cylinder via Tygon tubing that was inserted into the reaction flask via the rubber septum. Then, the addition of nitrogen dioxide begun and continue for two days, where the formation of a brown solid was observed. The hydrolysis of the product was done using 20 mL of hydrochloric acid (10% by volume), and 40 mL of water, after this the PH was slightly basic. The extraction was done three times using 30 mL of ether. The products of each layer were identified using GC/MS.

Aqueous layer: N-nitroso-isoproplyamine; isopropylamine.

Ether layer: N-nitroso-isopropylamine.

Example 5

This example illustrates the reaction between bis( N-ter-butyl-trimethyl silylamino)magnesium and $NO_2/N_2O_4$.

Into a 200 mL airless ware flask previously flushed with argon gas were transferred 50.0 mL (35.5 mmol) of a 0.71 M solution of dibutylmagnesium via syringe through a septum mounted on the reaction flask. Argon flow to the flask was stopped while 13.0 mL (72 mmol) of N-tert-butyl-trimethyl sylilamine was added dropwise to the dibutylmagnesium solution. Since there was no observable reaction, the reaction flask was heated with a reflux under argon for 15 h. Then it was observed a changed in color from clear to brown. After this reaction period, the reaction flask was connected to a nitrogen dioxide cylinder via Tygon tubing that was inserted into the reaction flask via the rubber septum. Then, the addition of nitrogen dioxide begun and continue for two days, where the formation of more brown solid was observed. The hydrolysis of the product was done using 20 mL of hydrochloric acid (10% by volume), and 40 mL of water, which was an exothermic reaction. After this the PH was slightly basic. The extraction was done three times using 30 mL of methylene chloride. The products of each layer were identified using GC/MS.

Aqueous layer; 2-methyl-propanamine.

Methylene chloride layer: trimethyl(1-methylpropoxy) silane; octamethyl-trisiloxane; N-(1,1-dimethylethyl) formamide; hexamethyl-disiloxane; 1,1,1,3,5,5,5-heptamethyl-trisiloxane; 1,1,3,3,5,5-hexamethyl-trisiloxane; 2,2,9,9-tetramethyl-3,8-dioxa-2,9-disiladecane.

Example 6

The example illustrates the reaction between bis((-)-cis-myrtanylamino)magnesium and $NO_2/N_2O_4$.

Into a 200 mL airless-ware flask previously purged with Ar were placed 28 mL (20 mmol) of dibutyl magnesium and 6 mL (40 mmol) of (-)-cis-myrtanylamine were added dropwise. The reaction mixture was allowed to react for 24 hrs, forming an orange solid. Then, the bubbling of $NO_2/N_2O_4$ started. The solution became brown. The hydrolysis was made with 20 mL of HCl (10%), and 40 mL of water, the pH was neutral. The extraction was done with ether, where 3 layers separated, the third layer was a red liquid denser than water, and partially soluble in ether. GC/MS results:

Aqueous layer: bicyclo[2.2.1]heptane-7,7-dimethyl-2-methylene; α-pinene; limonene; bornylchloride; cyclohexene; 1-methyl-4-(1-methylethylidene).

Ether layer: cyclohexane, 1-methylene-4-(1-methylethenyl); tricyclo[3.2.1.01,5]octane; bicyclo[3.1.1]heptan-2-one-6,6-dimethyl, (1R).

Third layer: β-pinene; bicyclo[2.2.1]heptane-7,7-dimethyl-2-methylene; cyclohexene, 1-methyl-4(1-methylethylidene); 2,4-hexadiene-2,5-dimethyl; 2-decyn-1-ol.

Example 7

This example illustrates the reaction between bis (dihexylamino)magnesium and $NO_2/N_2O_4$.

Into a 200 mL airless-ware flask previously purged with Ar were placed 50 mL (35.5 mmol) of dibutyl magnesium and 9.4 mL (71 mmol) of hexylamine were added dropwise. The reaction mixture was allowed to react for 24 hrs, forming a semi-solid solution of cream color. Then, the bubbling of $NO_2/N_2O_4$ started. The solution became orange. The hydrolysis was made with 20 mL of HCl (10%), the solution changed color from orange to green, it was an exothermic reaction, also there was more solid formed. Then, the hydrolysis continue adding 40 mL of water, the pH was basic. The extraction was done with ether. Part of the solid seemed to be dissolved in the ether.

GC/MS results

Aqueous layer: hexanenitrile; piperidine-5-ethyl-2-methyl; valeramide-N-hexyl; 1,2,4-cyclopentanetrione, 3-butyl.

Ether layer: hexylamine; hexanol; valeramide-N-hexyl.

Then HCl(10%) was added to neutralize the aqueous layer. The solid disappeared and the formation of two layers was observed. Then, the layers were extracted with ether again.

GC/MS results

Aqueous layer: hexanal; hexylamine.

Ether layer: hexanol; piperidine-5-ethyl-2-methyl; hexanoic acid, 2-propenyl ester.

Example 8

This example illustrates the reaction between bis(1-aminonaphthyl)magnesium with $NO_2/N_2O_4$.

Into a 200 mL airless-ware flask previously purged with Ar were placed 10.2 gr (71 mmol) of 1-aminonaphthalene and 50 mL (35.5 mmol) of dibutyl magnesium was added dropwise. The reaction mixture was allowed to react for 24 hrs, forming a solution of cream color. Then, the bubbling of $NO_2/N_2O_4$ started. The solution and part of the solid became very dark. The hydrolysis was made with 20 mL of HCl (10%), and 40 mL of water, the pH was basic. After the hydrolysis all the solid became very dark. The extraction was done with ether.

GC/MS results

Aqueous layer: 1-chloro-naphthalene; 1-naphthaleneamine.

Ether layer: naphthalene; 1-naphthaleneamine.

Example 9

This example illustrates the reaction of Bis(N,N-diethylamine)magnesium with $NO_2/N_2O_4$.

Into a 200 mL airless-ware flask previously purged with Ar were placed 50 mL (35.5 mmoles) of dibutyl magnesium and 7.5 mL (71 mmoles) of N,N-diethylamine was added dropwise. The reaction mixture was allowed to react for 24 hrs, forming a solution of cream color. Then, the bubbling of $NO_2/N_2O_4$ started. The solution and part of the solid became darker. The hydrolysis was made with 20 mL of HCl (10%), and 40 mL of water, the pH was basic. The extraction was done with ether.

GC/MS results

Aqueous layer: N,N-diethylamine; diethylamine-N-nitroso.

Ether layer: diethylamine-N-nitroso.

Example 10

This example illustrates the reaction of N-cyclohexylamine with dibutyl magnesium and then with $NO_2/N_2O_4$.

Into a 200 mL airless-ware flask previously purged with Ar were placed and 50 mL (35.5 mmoles) of dibutyl magnesium and 7.7 mL (71 mmoles) of N-cyclohexylamine was added dropwise. The reaction mixture was allowed to react for 24 hrs, forming a white solid immediately. Then, the bubbling of $NO_2/N_2O_4$ started. The solution and the solid turned creamed color. The hydrolysis was made with 20 mL of HCl (10%), and 40 mL of water, the pH was basic. The solution and the solid became darker (brown color). The extraction was done with ether.

GC/MS results

Aqueous layer: cyclohexanol; cyclohexanone; cyclohexanone oxime; N-cyclohexylamine.

Ether layer: N-cyclohexylamine.

Example 11

This example illustrates the reaction between bis(1-aminonaphthyl)magnesium and $NO_2/N_2O_4$ in the presence of the donor solvent, diethylether:

Into a 200 mL airless-ware flask previously purged with Ar were placed 50 mL (35.5 mmoles) of dibutyl magnesium and 10.2 g (71 mmoles) of 1-aminonaphthalene were added dropwise. The reaction mixture was allowed to react for 24 hrs. The liquid is cream color. Before the addition of $NO_2/N_2O_4$, 50 mL of ethyl ether were added. Then, the addition of $NO_2/N_2O_4$ started. The solution became very dark. The hydrolysis was made with 20 mL of HCl (10%), and 40 mL of water. The pH of the solution was neutral. The extraction was done with ether.

GC/MS results

Aqueous layer: 1-aminonaphthalene.

Ether layer: naphthalene; 1-aminonaphthalene.

Example 12

This example illustrates the reaction between bis (diisoprpylamino)magnesium and $NO_2/N_2O_4$ in the presence of a donor solvent:

Into a 200 mL airless-ware flask previously purged with Ar were placed 50 mL (35.5 mmoles) of dibutyl magnesium and 10 mL (71 mmoles) of diisopropylamine were added dropwise. The reaction mixture was allowed to react for 24 hrs. The liquid is cream color. Before the addition of $NO_2/N_2O_4$, 50 mL of ethyl ether were added. Then, the addition of $NO_2/N_2O_4$ started. The solution became brown. The hydrolysis was made with 20 mL of HCl (10%), and 40 mL of water, and 10 mL of NaOH (10%). The pH of the solution was basic. The extraction was done with ether.

GC/MS results

Aqueous layer: diisopropylamine-N-nitroso; diisopropylamine.

Ether layer: diisopropylamine-N-nitroso; diisopropylamine.

Although the invention has been disclosed with reference to its preferred embodiments, from reading this description those of skill in the art may appreciate changes and modifications that may be made which do not depart from the scope and spirit of the invention as described above and claimed hereafter.

We claim:

1. An organoaminomagnesium complex comprising a composition of formula (III):

$$[(R_2N)_i(R_2NN_xO_y)_j Mg]_m \tag{III}$$

where:

the R groups are the same or different and are hydrogen atoms, carbon containing groups or silicon containing groups;

i is a number having a value less than 2.0 (i<2.0);

j is a number having a value greater than 0.0 and less than or equal to 2.0 (0.0<j≦2.0);

m is an integer having a value between 1 and infinity (1≦m≦∞);

x is an integer having a value between 1 and about 8; and y is an integer having a value between 1 and about 16.

2. The complex of claim 1, wherein m is between 1 and about 100, i is 0.0 and j is 2.0, and x has a value of 1 or 2 and y has a value of 2 or 4 and the carbon containing group is a hydrocarbyl group, substituted or heteroatom analog thereof and the silicon containing group is a silylhydrocarbyl group, substituted or heteroatom analog thereof.

3. An organoaminomagnesium complex comprising compounds of formula (IIIa):

$$[(R_2N)_i(R_2NNO_2)_{ja}(R_2NN_2O_4)_{jb} Mg]_m \tag{IIIa}$$

where:

the R groups are the same or different and are hydrogen atoms, carbon containing groups or silicon containing groups;

i is a number having a value less than 2.0 (i<2.0);

ja and jb are numbers, the sum of which is greater than 0.0 and less than or equal to 2.0 (0.0<ja+jb≦2.0); and m is an integer having a value between 1 and infinity (1≦m≦∞).

4. The complex of claim 3, wherein m is between 1 and about 100, i is 0.0 and the sum of ja and jb is 2.0 and the carbon containing group is a hydrocarbyl group, substituted or heteroatom analog thereof and the silicon containing group is a silylhydrocarbyl group, substituted or heteroatom analog thereof.

5. An organoaminomagnesium complex comprising compounds of formula (IIIb):

$$[(R_2N)_i(R_2NNO_2)_j Mg]_m \tag{IIIb}$$

where:

the R groups are the same or different and are hydrogen atoms, carbon containing groups or silicon containing groups;

i is a number having a value less than 2.0 (i<2.0);

j is a number having a value greater than 0.0 and less than or equal to 2.0 (0.0<j≦2.0); and m is an integer having a value between 1 and infinity (1≦m≦∞).

6. The complex of claim 5, wherein m is between 1 and about 100, i is 0.0 and j is 2.0 and the carbon containing group is a hydrocarbyl group, substituted or heteroatom analog thereof and the silicon containing group is a silylhydrocarbyl group, substituted or heteroatom analog thereof.

7. An organoaminomagnesium complex comprising compounds of formula (IIIc):

$$[(R_2N)_i(R_2NN_2O_4)_j Mg]_m \tag{IIIc}$$

where:

the R groups are the same or different and are hydrogen atoms, carbon containing groups or silicon containing groups;

i is a number having a value less than 2.0 (i<2.0);

j is a number having a value greater than 0.0 and less than or equal to 2.0 (0.0<j≦2.0); and m is an integer having a value between 1 and infinity (1≦m≦∞).

8. The complex of claim 7, wherein m is between 1 and about 100, i is 0.0 and j is 2.0 and the carbon containing group is a hydrocarbyl group, substituted or heteroatom analog thereof and the silicon containing group is a silylhydrocarbyl group, substituted or heteroatom analog thereof.

9. An organoaminomagnesium complex comprising compounds of formula (IV):

$$[(R_2N)_i(R_2NN_xO_y)_j(N_xO_y)_kMg]_m \quad (IV)$$

where:
the R groups are the same or different and are hydrogen atoms, carbon containing groups or silicon containing groups;
i is a number having a value less than 2.0 (i<2.0);
j is a number having a value greater than or equal to 0.0 and less than or equal to 2.0 ($0.0 \leq j \leq 2.0$);
k is a number having a value less than 2.0 (k<2.0);
m is an integer having a value between 1 and infinity ($1 \leq m \leq \infty$);
x is an integer having a value between 1 and about 8; and
y is an integer having a value between 1 and about 16.

10. The complex of claim 9, wherein m is between 1 and about 100, i is about 0.0, k is about 0.0 and j is about 2.0 and the carbon containing group is a hydrocarbyl group, substituted or heteroatom analog thereof and the silicon containing group is a silylhydrocarbyl group, substituted or heteroatom analog thereof.

11. A process comprising the step of:
contacting a compound of formula (I):

$$[(R_2N)_2Mg]_n \quad (I)$$

with a compound of formula (II):

$$N_xO_y \quad (II)$$

to form a reaction mixture comprising intermediates of formulas (III) and (IV):

$$[(R_2N)_i(R_2NN_xO_y)_jMg]_m \quad (III)$$

$$[(R_2N)_i(R_2NN_xO_y)_j(N_xO_y)_kMg]_m \quad (IV)$$

under reaction conditions sufficient to facilitate the formation of the intermediates of formulas (III) and (IV), where:
the R groups are the same or different and are a hydrogen atom, a linear or branched carbon containing group or a linear or branched silicon containing group;
i is a number having a value less than 2.0 (i<2.0);
j is a number having a value greater than 0.0 and less than or equal to 2.0 ($0.0<j \leq 2.0$) for compounds of formula (III) and a value greater than or equal to 0.0 and less than or equal to 2.0 ($0.0 \leq j \leq 2.0$) for compounds of formula (IV);
k is a number having a value less than 2.0 (k<2.0);
n is an integer having a value between 1 and infinity ($1 \leq n \leq \infty$);
m is an integer having a value between 1 and infinity ($1 \leq m \leq \infty$);
x is an integer having a value between 1 and about 8; and
y is an integer having a value between 1 and about 16.

12. The method of claim 11, further comprising the step of:
converting the reaction mixture into nitrogen gas and nitrogen-free, combustible organic derivatives of the R group of the $R_2N$ moiety of formula (I).

13. The method of claim 11, further comprising the step of:
converting the reaction mixture into a reaction product comprising nitrosamine derivatives of the $R_2N$ moiety of formula (I).

14. The method of claim 11, further comprising the step of:
protonating the reaction product in the presence of an acid or a base to form oxygenated derivative of the R groups of the $R_2N$ moiety of formula (I).

15. The method of claim 11, wherein m is between 1 and about 100, i is 0.0, k is 0.0 and j is 2.0 and the carbon containing group is a hydrocarbyl group, substituted or heteroatom analog thereof and the silicon containing group is a silylhydrocarbyl group, substituted or heteroatom analog thereof.

16. A process comprising the steps of:
(a) contacting a scavenger comprising compounds of formula (I):

$$[(R_2N)_2Mg]_n \quad (I)$$

with a waste stream comprising compounds of formula (II):

$$N_xO_y \quad (II)$$

to form a reaction mixture comprising intermediates of formulas (III) and (IV):

$$[(R_2N)_i(R_2NN_xO_y)_jMg]_m \quad (III)$$

$$[(R_2N)_i(R_2NN_xO_y)_j(N_xO_y)_kMg]_m \quad (IV)$$

and an unreacted portion of the compounds of formula (I) under reaction conditions sufficient to facilitate the formation of the intermediates of formulas (III) and (IV); and
(b) separating the reaction mixture into an intermediate product comprising the compounds of formulas (III) and (IV) and unreacted compounds of formula (I);

where:
the R groups are the same or different and are a hydrogen atom, a linear or branched carbon containing group or a linear or branched silicon containing group;
i is a number having a value less than 2.0 (i<2.0);
j is a number having a value greater than 0.0 and less than or equal to 2.0 ($0.0<j \leq 2.0$) for compounds of formula (III) and a value greater than or equal to 0.0 and less than or equal to 2.0 ($0.0 \leq j \leq 2.0$) for compounds of formula (IV);
k is a number having a value less than 2.0 (k<2.0);
n is an integer having a value between 1 and infinity ($1 \leq n \leq \infty$);
m is an integer having a value between 1 and infinity ($1 \leq m \leq \infty$);
x is an integer having a value between 1 and about 8; and
y is an integer having a value between 1 and about 16.

17. The method of claim 16, further comprising the step of:
(c) recycling the unreacted compounds of formula (I) with the scavenger of step (a).

18. The method of claim 16,
(d) protonating the intermediate product to form a magnesium containing product and a nitrogen-free product comprising nitrogen-free derivative of R.

19. The method of claim 18, (e) regenerating a regenerated scavenger by contacting the magnesium containing product with a starting amine of formula $R_2NH$;

(f) combining the regenerated scavenger of step (e) with the scavenger of step (a); and (g) burning the nitrogen-free product of step (d) in the presence of an oxidizing agent to form combustion product comprising carbon dioxide and water substantially free of incomplete combustion products.

20. The method of claim 16, wherein the carbon containing group is a hydrocarbyl group, substituted or heteroatom analog thereof and the silicon containing group is a silylhydrocarbyl group, substituted or heteroatom analog thereof.

* * * * *